United States Patent
Wang et al.

(10) Patent No.: US 10,213,440 B2
(45) Date of Patent: *Feb. 26, 2019

(54) ORAL TRANSMUCOSAL PHARMACEUTICAL COMPOSITIONS INCLUDING TESTOSTERONE AND AN AROMATASE INHIBITOR

(71) Applicants: Tsu-I Catherine Wang, Sugar Land, TX (US); Bruce Vincent Biundo, Houston, TX (US)

(72) Inventors: Tsu-I Catherine Wang, Sugar Land, TX (US); Bruce Vincent Biundo, Houston, TX (US)

(73) Assignee: PROFESSIONAL COMPOUNDING CENTERS OF AMERICA (PCCA), Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/685,345

(22) Filed: Apr. 13, 2015

(65) Prior Publication Data

US 2016/0051563 A1 Feb. 25, 2016

Related U.S. Application Data

(60) Provisional application No. 62/039,814, filed on Aug. 20, 2014.

(51) Int. Cl.
| | |
|---|---|
| *A61K 9/00* | (2006.01) |
| *A61K 9/20* | (2006.01) |
| *A61K 47/10* | (2017.01) |
| *A61K 47/36* | (2006.01) |
| *A61K 47/38* | (2006.01) |
| *A61K 47/42* | (2017.01) |
| *A61K 31/568* | (2006.01) |
| *A61K 31/4196* | (2006.01) |

(52) U.S. Cl.
CPC ............ *A61K 31/568* (2013.01); *A61K 9/006* (2013.01); *A61K 9/0056* (2013.01); *A61K 9/2018* (2013.01); *A61K 31/4196* (2013.01); *A61K 47/10* (2013.01); *A61K 47/36* (2013.01); *A61K 47/38* (2013.01); *A61K 47/42* (2013.01)

(58) Field of Classification Search
CPC .... A61K 31/568; A61K 9/006; A61K 9/0056; A61K 9/2018; A61K 47/10; A61K 47/38; A61K 47/36; A61K 31/4196
See application file for complete search history.

(56) References Cited

U.S. PATENT DOCUMENTS

| | | | |
|---|---|---|---|
| 6,696,432 B1 | 2/2004 | Elliesen et al. | |
| 2003/0139384 A1* | 7/2003 | Dudley | A61K 9/0014 514/177 |
| 2004/0235812 A1* | 11/2004 | Caspers | A61K 31/4196 514/182 |
| 2005/0281172 A1* | 12/2005 | Wachi | G11B 7/1353 369/112.23 |
| 2009/0111736 A1* | 4/2009 | Shankar | A61K 9/2013 514/1.1 |
| 2009/0215731 A1* | 8/2009 | Birrell | A61K 31/4196 514/170 |
| 2010/0144687 A1 | 6/2010 | Glaser | |
| 2012/0122824 A1* | 5/2012 | Birrell | A61K 31/4196 514/170 |
| 2014/0079756 A1 | 3/2014 | Andersen et al. | |
| 2014/0112986 A1 | 4/2014 | Betageri et al. | |
| 2014/0162991 A1 | 6/2014 | Glaser | |
| 2015/0065426 A1 | 3/2015 | Wang et al. | |

FOREIGN PATENT DOCUMENTS

WO PCT/US2015/045912 11/2015

OTHER PUBLICATIONS

Sharma et a. (Pharmazie 61: 495-504 (2006).*
Brown et al. (J. Appl. Physiol.. 92: 142-146, 2002).*
Biundo (Int. J. of Pharmaceutical Componding; 17(1) (Jan./Feb. 2013) and Birrell (US 2012/0122824).*
Basil et al (Therapeutic Clinical Risk Management (2009); 5; 427-448).*
Ronde et al. (Reproductive Biology and endocrineology (2011); 993 pp. 1-7).*
Orwoll et al. (the J. of Clinical Endocrinology and Metabolism 92(4):1336-1344).*
Glaser et al., (2014) "Rapid response of breast cancer to neoadjuvant intramammary testosterone-anastrozole therapy: neoadjuvant hormone therapy in breast cancer." Menopause 21, 6: 673-678.
Glaser et al. (2013) "Reduced breast cancer incidence in women treated with subcutaneous testosterone, or testosterone with anastrozole: a prospective, observational study." Maturitas 76, 4: 342-349.

(Continued)

*Primary Examiner* — Shirley V Gembeh
(74) *Attorney, Agent, or Firm* — David G. Woodral; GableGotwals

(57) ABSTRACT

Formulations for oral transmucosal compositions including a synergistic combination of low doses of testosterone with an aromatase inhibitor (AI) that are combined with transmucosal absorption enhancers are disclosed. Oral transmucosal compositions can be for fast release or slow release, and can be administered to increase bloodstream testosterone levels and thereby reduce symptoms of testosterone deficiency. Oral transmucosal compositions include liquid dosage forms, solid dosage forms, and chewing gums. Further dosage forms include mucoadhesive thin strips, thin films, tablets, patches, and tapes, among others. Other dosage forms are: mucoadhesive liquids such as gel-forming liquids; gel-forming semisolids; and gel-forming powders, among other dosage forms that exhibit mucoadhesive properties, and provide oral transmucosal delivery of testosterone and AI. Oral transmucosal compositions will deliver testosterone and AI directly into the patient's bloodstream, and provide high bioavailability of testosterone and AI; therefore, the required doses are lower.

16 Claims, No Drawings

(56) References Cited

OTHER PUBLICATIONS

Rhoden and Morgentaler (2004) "Treatment of testosterone-induced gynecomastia with the aromatase inhibitor, anastrozole" International Journal of Impotence Research 16, 95-97.

* cited by examiner

ORAL TRANSMUCOSAL PHARMACEUTICAL COMPOSITIONS INCLUDING TESTOSTERONE AND AN AROMATASE INHIBITOR

CROSS-REFERENCE TO RELATED APPLICATIONS

This application claims priority to U.S. Provisional Application Ser. No. 62/039,814, filed Aug. 20, 2014, which is hereby incorporated by reference.
N/A

BACKGROUND

Field of the Disclosure

The present disclosure relates generally to pharmaceutical compositions, and more particularly, to oral transmucosal pharmaceutical compositions including testosterone synergistically combined with an aromatase inhibitor (AI) for testosterone deficiency and to maintain estradiol within normal physiologic levels.

Background Information

Testosterone is the androgenic hormone primarily responsible for normal growth and development of male sex and reproductive organs, including the penis, testicles, scrotum, prostate, and seminal vesicles. Testosterone facilitates the development of secondary male sex characteristics such as musculature, bone mass, fat distribution, hair patterns, laryngeal enlargement, and vocal cord thickening, among others. Additionally, normal testosterone levels maintain energy level, healthy mood, fertility, and sexual desire.

The production of testosterone by the testes is regulated by a complex chain of signals that begins in the brain, mediated by the hypothalamic-pituitary-gonadal axis. The hypothalamus secretes gonadotropin-releasing hormone (GnRH) to the pituitary gland in pulses (bursts) which triggers the secretion of luteinizing hormone (LH) from the pituitary gland. Luteinizing hormone stimulates the Leydig cells of the testes to produce testosterone. Normally, the testes produce approximately 4 mg to 7 mg of testosterone per day.

Generally speaking, testosterone production declines naturally with age. In addition, low testosterone, or testosterone deficiency (TD), may result from disease or damage to the hypothalamus, pituitary gland or testicles that inhibits hormone secretion and testosterone production, and is also known as hypogonadism. Depending on age, insufficient testosterone production can lead to abnormalities in muscle and bone development, underdeveloped genitalia and diminished virility.

Currently, the most common treatment for symptomatic male testosterone deficiency is testosterone therapy with various transdermal, oral, buccal, and injectable delivery methods. These methods typically involve very high doses of testosterone. The main purpose of the testosterone replacement therapy is to achieve normal range of testosterone serum levels.

Oral therapy of testosterone lacks effectiveness because testosterone is metabolized extensively during the first passage of the liver before reaching the systemic blood circulation (e.g., the first-pass effect). Intramuscular injections of testosterone esters are widely used, but local pain, tolerability, and the unphysiologically high levels of testosterone in the body during the first days/weeks after injection are severe drawbacks to this form of treatment. Local pain is attributed to the large volumes of testosterone injected and the required help of health care professionals makes injections inconvenient and expensive. These same drawbacks also apply to implanted pellets.

Transdermal administration (e.g., patches, gels, etc.) has the benefit that the first-pass effect is avoided and the treatment is not painful. Unfortunately, transdermal compositions, excluding patches, currently prescribed for hypogonadal men include from 40 mg to 120 mg daily doses of which only a low percentage is absorbed through the skin. Another drawback is that a large part of the testosterone remains on the skin with the potential risk of being transferred to another person when direct skin-to-skin contact is made. Additionally, the non-absorbed portion of testosterone is lost to the surrounding environment making these formulations non-environmentally-friendly. Additionally, a common side effect of transdermal compositions is local skin irritation. This is likely due to the very high ethanol content of such formulations.

Oral transmucosal delivery is a particularly advantageous delivery route. One of the advantages of oral transmucosal delivery is that it is a non-invasive drug delivery method. It promotes better patient compliance and involves lower costs than invasive procedures such as injection and implantation. Oral transmucosal delivery also results in much shorter onset time (e.g., the time from administration to therapeutic effect) than oral delivery does and may be easily self-administered. Oral transmucosal administration involves the patient holding the composition in the oral cavity while the API dissolves in the available fluid, diffuses through the mucosa lining of the mouth, and enters the bloodstream bypassing the gastrointestinal tract as well as hepatic metabolism.

Recently, research studies have demonstrated that aromatase inhibitors (AIs) as APIs may be used to treat low testosterone levels in men. AIs work by binding to the aromatase and inhibiting this enzyme that converts testosterone into estrogen. Estradiol serves as a major mediator of sex steroid-gonadotropin feedback; hence, high estradiol levels could contribute to low testosterone production through inhibition of LH. Meanwhile, high estradiol levels can also exist independently of testosterone levels. AIs effectively inhibit or block conversion of testosterone into estrogen which leads to increased LH and follicle-stimulating hormone (FSH) release from the pituitary. Increased LH and FSH results in a subsequent increase in testicular stimulation and serum testosterone levels without the increase in estrogen levels, and thus could limit the likelihood of undesirable effects such as gynecomastia. However, there are no AI products on the market that are indicated for treatment of testosterone deficiency while maintaining physiologic levels of estradiol.

SUMMARY

The present disclosure refers to oral transmucosal compositions that include a synergistic combination of low doses of testosterone with an aromatase inhibitor (AI) in order to increase testosterone levels in a patient's bloodstream and reduce symptoms of testosterone deficiency. The synergistic combination of low doses of testosterone and AI may lead to increased levels of testosterone in the patient without the side effect of high estrogen levels. As such, oral transmucosal compositions can be used in treating a wide variety of conditions resulting from testosterone deficiency in men.

According to some embodiments, APIs include low doses of testosterone synergistically combined with an AI, such as anastrozole (Arimidex®), letrozole (Femara®), exemestane (Aromasin®), vorozole (Rivizor®), formestane (Lentaron®), fadrozole (Afema®), testolactone (Teslac®), or any other chemical compound that exhibits aromatase inhibition.

In an example, the AI employed in oral transmucosal compositions is anastrozole or chrysin.

In other embodiments, testosterone can be administered in the form of a testosterone ester. Examples of testosterone esters include testosterone cypionate, testosterone propionate, testosterone enanthate, testosterone heptylate, testosterone caproate, testosterone phenylpropionate, testosterone isocaproate, testosterone decanoate, testosterone acetate, testosterone laurate, or a pharmaceutically acceptable ester thereof, or any combination thereof.

In some embodiments, various additives are included to facilitate the preparation of suitable dosage forms. For example, additives include solvents, diluents, binders, disintegrants, lubricants, glidants, mucoadhesive polymers, thickening agents, transmucosal absorption enhancers, polymer plasticizers, pH adjusters, preservatives, sweeteners, flavors, colors, effervescent agents, stabilizing agents, antioxidants, and surfactants, among others.

In some embodiments, transmucosal absorption enhancers provide more efficient penetration of APIs through oral mucosal tissue. In these embodiments, the transmucosal absorption enhancers allow lower APIs dosage requirements.

In some embodiments, amount of absorption enhancers included in oral transmucosal compositions range from about 0.1% to about 20%; most suitable amount is of about 1% to about 10%. These percent ranges may refer to % weight by weight, % weight by volume, or % volume by volume.

In some embodiments, oral transmucosal compositions allow the delivery of testosterone and AI directly into the patient's bloodstream bypassing the gastrointestinal tract and the hepatic metabolism. In these embodiments, oral transmucosal compositions will provide higher percentages of bioavailability of testosterone and AI to the patient, and this also allows lower dosage requirements of testosterone.

In some embodiments, oral transmucosal compositions are administered in the oral cavity at the sublingual, palatal, buccal, gingival, or the like.

In some embodiments, oral transmucosal compositions may be tailored for individual patients according to clinical symptoms and baseline serum concentrations of testosterone and estradiol. These oral transmucosal compositions may be prescribed with various concentrations of testosterone and AI, and suitable dosage regimens to more closely mimic the circadian rhythm and physiological pulsatile secretion of testosterone, thereby keeping the testosterone and estradiol levels within physiologic range.

In an example, oral transmucosal compositions are administered at a dosage range of about 25 mg/day to about 100 mg/day of testosterone, preferably of about 25 mg/day to about 50 mg/day; and of about 0.05 mg/day to about 1.0 mg/day of anastrozole, preferably about 0.1 mg/day to about 0.5 mg/day.

In another example, oral transmucosal compositions are administered at a dosage range of about 25 mg/day to about 100 mg/day of testosterone, preferably of about 25 mg/day to about 50 mg/day; and of about 5 mg/day to about 100 mg/day of chrysin, preferably about 10 mg/day to about 25 mg/day.

According to some embodiments, oral transmucosal compositions include different components, such as active pharmaceutical ingredients (APIs), transmucosal absorption enhancers, suitable vehicles, and suitable additives, among others.

In some embodiments, oral transmucosal compositions include liquid dosage forms such as sublingual solutions, emulsions, suspensions, and liquid sprays, among others. In other embodiments, oral transmucosal compositions include solid dosage forms such as sublingual tablets, and buccal troches, among others. In yet other embodiments, oral transmucosal dosage forms include chewing gums.

In some embodiments, oral transmucosal dosage forms include mucoadhesive polymers as part of the compositions. Examples of dosage forms include mucoadhesive thin strips, thin films, tablets, patches, and tapes, among others. In other embodiments, dosage forms include: mucoadhesive liquids such as gel-forming liquid; semisolids such as gels, gel-forming ointments, and gel-forming pastes; gel-forming powders, or any other dosage forms that exhibit mucoadhesive properties and provide oral transmucosal delivery of testosterone and AI.

In some embodiments, low dose APIs in any of the above identified dosage forms may result in acceptable testosterone levels in the patient. This contrasts with current popular topical treatment options which use very high dosages of testosterone to get a few milligrams of testosterone absorbed into the bloodstream.

In some embodiments, oral transmucosal dosage forms are designed for fast release and transmucosal absorption of testosterone and AI. In other embodiments, oral transmucosal dosage forms are designed for slow release and absorption of testosterone and AI over a prolonged period of time.

Numerous other aspects, features, and benefits of the present disclosure may be made apparent from the following detailed description.

DETAILED DESCRIPTION

The present disclosure is described here in detail. Other embodiments may be used and/or other changes may be made without departing from the spirit or scope of the present disclosure. The described embodiments are not meant to limit the subject matter presented here.

Definitions

As used here, the following terms have the following definitions:

"Active Pharmaceutical Ingredients (APIs)" refer to chemical compounds that induce a desired effect, and include agents that are therapeutically or prophylactically effective.

"Absorption Enhancer" or, equivalently, "Penetration Enhancer" refers to a substance used to increase the rate of permeation through the mucous membrane, skin or other body tissue of one or more substances (e.g., APIs) in a formulation.

"Aromatase Inhibitors (AIs)" refer to chemical compounds that block or inhibit the activity of aromatase which is an enzyme that converts androgens to estrogens. As such, an aromatase inhibitor acts to reduce estrogen levels in the body.

"Treating" and "Treatment" refers to reduction in severity and/or frequency of symptoms, elimination of symptoms and/or underlying cause, prevention of the occurrence of symptoms and/or their underlying cause, and improvement or remediation of damage.

"Vehicle" refers to a substance of no therapeutic value that is used to convey at least one API for administration.

Description of the Disclosure

The present disclosure is directed towards oral transmucosal compositions that include synergistic combinations of low doses of testosterone and AI as APIs. These oral transmucosal compositions are proposed to increase testosterone levels, maintain estradiol levels within physiologic range, and reduce symptoms of testosterone deficiency in men without the side effect of high estrogen levels.

Estradiol serves as a major mediator of sex steroid-gonadotropin feedback; hence, high estradiol levels could contribute to low testosterone production through inhibition of luteinizing hormone (LH). Aromatase inhibitors block the formation of estradiol from testosterone and can limit the inhibition of LH. High estradiol levels can exist independently of testosterone levels and AIs may limit the likelihood of undesirable effects from estradiol such as gynecomastia.

Formulation

Oral transmucosal compositions include a synergistic combination of low doses of testosterone with AI as APIs, transmucosal absorption enhancers, vehicles, and additives, among other suitable ingredients.

According to some embodiments, APIs include low doses of testosterone synergistically combined with an AI, such as, anastrozole (Arimidex®), letrozole (Femara®), exemestane (Aromasin®), vorozole (Rivizor®), formestane (Lentaron®), fadrozole (Afema®), testolactone (Teslac®), or any other chemical compound that exhibits aromatase inhibition.

In an example, the AI employed in oral transmucosal compositions is anastrozole or chrysin.

In other embodiments, testosterone can be administered in the form of a testosterone ester. Examples of testosterone esters include testosterone cypionate, testosterone propionate, testosterone enanthate, testosterone heptylate, testosterone caproate, testosterone phenylpropionate, testosterone isocaproate, testosterone decanoate, testosterone acetate, testosterone laurate, or a pharmaceutically acceptable ester thereof, or any combination thereof.

The synergistic effect between low doses of testosterone and AI may lead to increased levels of testosterone in the patient without side effect of high estrogen levels. Therefore, oral transmucosal compositions can be used in treating a wide variety of conditions resulting from testosterone deficiency in men.

In some embodiments, various additives are included to facilitate the preparation of suitable dosage forms. For example, additives include solvents, diluents, binders, disintegrants, lubricants, glidants, mucoadhesive polymers, thickening agents, transmucosal absorption enhancers, polymer plasticizers, pH adjusters, preservatives, sweeteners, flavors, colors, effervescent agents, stabilizing agents, antioxidants, and surfactants, among others.

In some embodiments, diluents for solid dosage forms include calcium carbonate, dibasic calcium phosphate, tribasic calcium phosphate, calcium sulfate, kaolin, microcrystalline cellulose, and other cellulose derivates, sodium chloride, starch and starch derivates, sucrose, dextrose, lactose, and sorbitol, among others.

Binders for solid dosage forms include starch and starch derivatives, gelatin, sucrose, glucose, dextrose, molasses, lactose, natural and synthetic gums, acacia, sodium alginate, extract of Irish Moss, panwar gum, ghatti gum, mucilage of isapol husks, carboxymethylcellulose, methylcellulose, cellulose derivatives, Veegum, polyvinylpyrolidone, and polyethylene glycols, among others.

Disintegrants for solid dosage forms include veegum, agar, bentonite, alginic acid and alginic acid derivatives, guar gum, starch, sodium starch glycolate, other starch derivatives, clays, cellulose, and cellulose derivatives, among others.

Lubricants for solid dosage forms include stearic acid, stearic acid derivatives, stearic acid salts such as magnesium stearate and calcium stearate, talc, hydrogenated vegetables oils, polyethylene glycols, surfactants, and waxes, among others.

Additionally, solid dosage forms of oral transmucosal compositions include: a glidant, such as colloidal silicon dioxide and talc, among others; a sweetening agent, such as sucrose or saccharin, among others; natural or artificial flavors, such as peppermint, methyl salicylate, or orange flavor, among others.

The pH adjusting agents include sodium bicarbonate, magnesium hydroxide, calcium carbonate, dibasic calcium phosphate, tribasic calcium phosphate, sodium bicarbonate, magnesium hydroxide, potassium hydroxide, citric acid, lactic acid, hydrochloric acid, sulfuric acid, phosphoric acid, sodium phosphate monobasic, and sodium phosphate dibasic, among others.

Surfactants include: polysorbates such as polysorbate 20, 40, 60, and 80, among others; sorbitan esters such as sorbitan monolaurate, and sorbitan monopalmitate, sorbitan monooleate, among others; and sodium lauryl sulfate, among others.

Effervescent agents are usually a combination of one or more acids with one or more bases. Acids are selected from citric acid, tartaric acid, and the like. Bases can be sodium bicarbonate or other suitable agents that may react with acids, and produce gas.

In some embodiments, a stabilizing agent is used to stabilize the API for a specific dosage form. In these embodiments, the stabilizing agent used will depend on the API used as well as the other additive ingredients. Any suitable chemical substance may be used as a stabilizing agent. Stabilizing agents are known to those skilled in the art and therefore will not be discussed further herein.

Mucoadhesive polymers include: gums such as acacia, agarose, alginic acid, sodium alginate and other alginic acid derivatives, carrageenan, gelatin, gellan, guar gum, hakea gum, karaya gum, and locust bean gum, among others; chitosan and chitosan derivatives; hyaluronic acid, pectin, and other polysaccharides; gelatin, polyisoprene, polyisobutylene, polyetherurethane, polyvinylalcohol, polyvinylpyrrolidone, polycarbophil, polyethylene oxide polymers, and pullulan, among others. Mucoadhesive polymers also include cellulose derivatives such as ethyl cellulose, cellulose acetate, hydroxyethyl cellulose, hydroxypropylcellulose, hydroxypropylmethylcellulose, methylcellulose, methylhydroxyethylcellulose, and sodium carboxymethyl cellulose, among others; poly(acrylic acid)-based polymers such as polyacrylates, poly(methylvinylether-co-methacrylic acid), poly(acrylic acid-co-ethylhexylacrylate), poly (acrylic acid-co-acrylamide), poly(acrylic acid-co-butylacrylate), poly(acrylic acid-co-methyl methacrylate), poly (2-hydroxyethyl methacrylate), polymethacrylates, poly (alkylcyanoacrylate) and other cyanoacrylates, poly (isohexycyanoacrylate), poly(isobutylcyanoacrylate), and hydroxyethyl methacrylate, and any other polymer known to a person skilled in the art that exhibits mucoadhesive characters.

Plasticizers for mucoadhesive polymeric dosage forms include pullulan, hydroxypropyl methylcellulose, propylene glycol, glycerol, sorbitol, mannitol, polyethylene glycols (PEG 200, 400, 600, 1000, 1500, 2000), tartaric acid, malic acid, lactic acid, citric acid, and yonkenafil, and any other chemical known to a person skilled in the art that can increase the plasticity of any mucoadhesive polymer.

In some embodiments, transmucosal absorption enhancers provide more efficient penetration of APIs through oral mucosal tissue. In these embodiments, the transmucosal absorption enhancers allow lower APIs dosage requirements.

Oral transmucosal absorption enhancers include: enzyme inhibitors such as aprotinin and puromycin, among others; chitosan and chitosan derivatives such as chitosan glutamate, trimethyl chitosan, chitosan-4-thioglycolic acid, 5-methyl-pyrrolidine chitosan, and chitosan-4-thio-butyl-amidine, among others; alpha, beta, and gama cyclodextrins such as dimethyl cyclodextrin, sulfobutyl cyclodextrin, 2-hydroxypropyl-beta-cyclodextrin, poly-beta-cyclodextrin, and methylated beta-cyclodextrin, among others; bile salts such as sodium deoxycholate, sodium glycocholate, sodium glycodeoxycholate, sodium glycodihydrofusidate, sodium taurocholate, sodium taurodeoxycholate, sodium taurogly-cocholate, sodium taurodihydrofusidate, and sodium urso-cholate, among others; chelating agents such as sodium EDTA, citric acid, sodium citrate, sodium salicylate, methylsalicylate, methoxysalicylate, and polyacrylates, among others; alcohols such as ethanol and isopropanol, among others; fatty acids and derivatives such as oleic acid, methyloleate, capric acid, neodecanoic acid, elaidic acid, lauric acid, palmitoylearnitine, cod liver oil extract, mono glycerides and diglycerides of oleic acid and capric acid, lauric acid, sodium laurate, linoleic acid, sodium fusidate, sodium caprate, lyceryl monolaurate, glyceryl monooleate, glyceryl monostearate, sucrose fatty acid esters, and diethylene glycol monoethyl ether, among others; lecithins and phospholipids such as phodphatidylcholine, lysophosphatidyl choline, and didecanoylphophatidylcholine, among others; sulfoxides such as dimethylsulfoxide and decylmethyl sulfoxide, among others; polyols such as glycerin, propylene glycol, propanediol, and polyethylene glycols of various molecular weights, among others; urea and derivatives such as unsaturated cyclic urea, among others; surfactants such as sodium dodecyl sulfate, sodium lauryl sulfate, dioctyl sodium sulfosuccinate, nonylphenoxypolyoxyethylene, polyoxyethylene alkyl ethers, polyoxyethylene-9-lauryl ether, polyoxyethylene 23 lauryl ether, polyoxyethylene-20-cetyl ether, polyethyleneglycol dodecyl ether, polyethylene glycol-8 laurate, glyceryl monolaurate, polyoxyethylene stearates, polysorbates, sorbitan fatty acid esters, polyoxyethylene castor oil derivatives, benzalkonium chloride, cetylpyridinium chloride, and cetyltrimethylammonium bromide, among others. Other oral transmucosal absorption enhancers include alkylglycosides, azone, hyaluronic acid, sodium Hyaluronate, glycine chenodeoxycholate, lauroyl macroglycerides, isopropyl myristate, isopropyl palmitate, glutathione, witepsol, menthol, capsaicin, taurine, tocopheryl acetate, lauroyl macroglycerides, lionoleoyl polyoxyl-6 glycerides; diethylene glycol monoethyl ether, dextran sulfate, various saponins, poly-l-arginine, and l-lysine, and any other chemical known to a person skilled in the art that exhibits penetration enhancing effect on transmucosal absorption.

In some embodiments, amount of absorption enhancers included in oral transmucosal compositions range from about 0.1% to about 20%; most suitable amount is of about 1% to about 10%. These percent ranges may refer to % weight by weight, % weight by volume, or % volume by volume.

Bases for chewing gum include cellulosic polymer, and acrylic polymer, among others.

In some embodiments, oral transmucosal compositions include pharmaceutical solvents to produce sprays, solutions, emulsions, suspensions, gels, gel-forming liquids, ointments and pastes, among others.

In some embodiments, pharmaceutical solvents for liquid dosage forms of oral transmucosal compositions include water, liquid polyethylene glycols of various molecular weights, ethyl oleate, medium chain triglycerides, isopropyl myristate, isopropyl palmitate, isopropyl stearate, other pharmaceutically acceptable esters of C8-C22 fatty acids and C2-C6 alcohols, mineral oil, and vegetable oils, among others.

C8-C22 fatty acids include fatty acids having from 8 to 22 carbon atoms, such as myristic acid, palmitic acid, stearic acid, arachidic acid, or oleic acid, among others.

C2-C6 alcohols include alcohols having from 2 to 6 carbon atoms, in particular the C2-C5 alcohols as well as the homologues with 6 carbon atoms including diols and triols such as ethanol, propylene glycol, and glycerol, among others.

Examples of vegetable oils include almond oil, peanut oil, sesame oil, sunflower oil, safflower oil, canola oil, corn oil, and olive oil, among others.

In some embodiments, oral transmucosal ointments and pastes include petrolatum, PCCA Plasticized™ base, paraffin wax, various synthetic wax, lanolin, beeswax, carnauba wax, candelila wax, silicones, isopropylesters, polyols, cellulose ethers, among other suitable bases. In addition, ointment bases also include suitable pharmaceutical solvents, such as water, liquid polyethylene glycols of various molecular weights, ethyl oleate, medium chain triglycerides, isopropyl myristate, isopropyl palmitate, isopropyl stearate, and other pharmaceutically acceptable esters of C8-C22 fatty acids and C2-C6 alcohols, mineral oil, and vegetable oils, among others.

Administration

In some embodiments, oral transmucosal compositions allow the delivery of testosterone with AI directly into the patient's bloodstream bypassing the gastrointestinal tract and the hepatic metabolism and will result in a higher percentage of bioavailability of the APIs to the patient, and this also allows lower dosage requirements of testosterone.

In some embodiments, oral transmucosal compositions are administered in the oral cavity at the sublingual, palatal, buccal, gingival, or the like. Oral transmucosal compositions may be self-administered by the patient or administered by a medical practitioner, such as a physician or nurse.

In some embodiments, oral transmucosal compositions include liquid dosage forms such as sublingual solutions, emulsions, suspensions, and liquid sprays, among others. In other embodiments, oral transmucosal compositions include solid dosage forms such as sublingual tablets, and buccal troches, among others. In yet other embodiments, oral transmucosal dosage forms include chewing gums.

In some embodiments, oral transmucosal dosage forms include mucoadhesive polymers as part of the compositions. Examples of dosage forms include mucoadhesive thin strips, thin films, tablets, patches, and tapes, among others. In other embodiments, dosage forms include: mucoadhesive liquids such as gel-forming liquids; semisolids such as gels, gel-forming ointments, and gel-forming pastes; gel-forming powders, or any other dosage forms that exhibit mucoadhesive properties and provide oral transmucosal delivery of APIs.

In some embodiments, oral transmucosal dosage forms are designed for fast release and transmucosal absorption of testosterone and AI. In other embodiments, oral transmucosal dosage forms are designed for slow release and absorption of testosterone and AI over a prolonged period of time.

In some embodiments, oral transmucosal compositions are administered in a single administration whereby a certain amount of testosterone and AI is administered at once. In an example, one puff of a spray solution is administered representing the full desired dose. In other embodiments, oral transmucosal compositions are administered by multiple administrations in one or more sub-doses over a specified period of time. In an example, one, two or more puffs of a smaller dose is administered preferably shortly after one another.

In some embodiments, oral transmucosal compositions may be tailored for individual patients according to clinical symptoms and baseline serum concentrations of testosterone and estradiol. These oral transmucosal compositions may be prescribed with various concentrations of testosterone and AI, and suitable dosage regimens to more closely mimic the circadian rhythm and physiological pulsatile secretion of testosterone, thereby keeping the testosterone and estradiol levels within physiologic range.

In some embodiments, low dose APIs in any of the above identified dosage forms may result in acceptable testosterone levels in the patient. This contrasts with current popular topical treatment options, which use very high dosages of testosterone to get a few milligrams of testosterone absorbed into the bloodstream.

In some embodiments, the dosages (e.g., daily) required depend on the type of AI included in the disclosed oral transmucosal compositions. In other words, some AIs are more potent than others, and hence, the dosing can vary among the various AIs used.

In an example, oral transmucosal compositions are administered at a dosage range of about 25 mg/day to about 100 mg/day of testosterone, preferably of about 25 mg/day to about 50 mg/day; and of about 0.05 mg/day to about 1.0 mg/day of anastrozole, preferably about 0.1 mg/day to about 0.5 mg/day.

In another example, oral transmucosal compositions are administered at a dosage range of about 25 mg/day to about 100 mg/day of testosterone, preferably of about 25 mg/day to about 50 mg/day; and of about 5 mg/day to about 100 mg/day of chrysin, preferably about 10 mg/day to about 25 mg/day.

The following examples are intended to illustrate the scope of the disclosure and are not intended to be limiting. It is to be understood that other pharmaceutical formulations known to those skilled in the art may alternatively be used.

EXAMPLES

Exemplary dosage forms of the oral transmucosal compositions are described below.

Example #1 illustrates formula for one sublingual tablet

| Ingredient | Composition |
| --- | --- |
| Anastrozole | 0.1 mg |
| Testosterone | 25 mg |
| Penetration enhancer(s) | 1-10% |
| Flavor(s) | 0.5-5% |
| Lactose/sucrose (80:20) | q.s. 150-200 mg |

Example #2 illustrates formula for one dose of sublingual drops

| Ingredient | Composition |
| --- | --- |
| Anastrozole | 0.1 mg |
| Testosterone | 25 mg |
| Co-solvent(s) | 10-50% |
| Penetration enhancer(s) | 1-10% |
| Flavor(s) | 0.5-5% |
| Sweetener(s) | 0.1-1.5% |
| Base Solvent | q.s. 0.1-0.2 mL |

Example #3 illustrates formula for one dose of oral adhesive paste

| Ingredient | Composition |
| --- | --- |
| Anastrozole | 0.1 mg |
| Testosterone | 25 mg |
| Gelatin | 1-5% |
| Pectin | 1-5% |
| Sodium Carboxymethylcellulose | 1-10% |
| Xanthan gum | 0.1-5% |
| PEG-90M | 1-10% |
| Penetration enhancer(s) | 1-10% |
| Flavor(s) | 0.5-5% |
| Sweetener(s) | 0.1-1.5% |
| PCCA Plasticized ™ Base* | q.s. 0.2-0.5 mL |

*It is a proprietary gel base produced by Professional Compounding Centers of America (PCCA)

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A method comprising:
   measuring a first blood serum concentration of testosterone and estradiol of a male patient;
   formulating a composition consisting of a mucosal penetration enhancer, a sugar, a solvent, and active pharmaceutical ingredients (APIs) consisting of anastrozole and testosterone present in amounts intended to restore the testosterone level of the patient to a physiologic range based on a deficiency determined from the first measured blood serum concentration of testosterone and anastrozole; and
   delivering the composition to an oral mucosal lining of the patient for a sufficient amount of time for diffusing said APIs through the mucosal lining of the oral cavity and into the bloodstream of the patient.

2. The method according to claim 1, wherein the anastrozole is present at about 0.1 mg.

3. The method according to claim 1, wherein the testosterone is present at about 25 mg.

4. The method according to claim 1, wherein the penetration enhancer is present at about 1.0% to about 10% by weight.

5. The method according to claim 4, wherein the penetration enhancer is selected from the group consisting of alkylglycosides, azone, hyaluronic acid, sodium Hyaluronate, glycine chenodeoxycholate, lauroyl macroglycerides, isopropyl myristate, isopropyl palmitate, glutathione, witepsol, menthol, capsaicin, taurine, tocopheryl acetate, lauroyl macroglycerides, lionoleoyl polyoxyl-6 glycerides; diethylene glycol monoethyl ether, dextran sulfate, various saponins, poly-I-arginine, and I-lysine.

6. The method according to claim 1, wherein the sugar is present at about 150 mg to about 200 mg.

7. The method according to claim 1, wherein the at least one solvent is present at about 10.0% to about 50.0% by weight.

8. The method according to claim 1, wherein the at least one solvent is selected from the group consisting of liquid polyethylene glycols of various molecular weights, ethyl oleate, medium chain triglycerides, isopropyl myristate, isopropyl palmitate, isopropyl stearate, pharmaceutically acceptable esters of C8-C22 fatty acids and C2-C6 alcohols, mineral oil, vegetable oil, and combinations thereof.

9. A method of increasing a level of testosterone in a male patient's bloodstream, comprising:
   measuring a first blood serum concentration of testosterone and estradiol of the male patient; and
   administering together, transmucosally, a composition comprising testosterone, anastrozole, and an oral mucosal penetration enhancer, wherein said testosterone and anastrozole enter the male patient's bloodsteam transmucosally apart from the male patient's gastrointestinal tract and the composition does not include estrogen;
   wherein said testosterone and anastrozole are administered into the patient's bloodstream in a dosage mimicking a physiological pulsatile secretion intended to provide blood serum testosterone and estradiol levels within physiologic range based upon the first measured blood serum concentration of testosterone and estradiol.

10. The method according to claim 9, wherein the anastrozole is present at about 0.1 mg.

11. The method according to claim 9, wherein the testosterone is present at about 25 mg.

12. The method according to claim 9, wherein the penetration enhancer is present at about 1.0% to about 10% by weight.

13. The method according to claim 12, wherein the penetration enhancer is selected from the group consisting of alkylglycosides, azone, hyaluronic acid, sodium Hyaluronate, glycine chenodeoxycholate, lauroyl macroglycerides, isopropyl myristate, isopropyl palmitate, glutathione, witepsol, menthol, capsaicin, taurine, tocopheryl acetate, lauroyl macroglycerides, lionoleoyl polyoxyl-6 glycerides; diethylene glycol monoethyl ether, dextran sulfate, various saponins, poly-I-arginine, and I-lysine.

14. The method of claim 9 wherein said testosterone is in the form of a testosterone ester.

15. The method of claim 1, further comprising:
   following the step of delivering the composition, determining a second blood serum level of testosterone and estradiol of the patient;
   reformulating the composition to create a reformulated composition having at least anastrozole and testosterone present in amounts intended to maintain the testosterone level of the patient in a physiologic range; and
   delivering the reformulated composition to the oral mucosal lining of the patient or second oral mucosal lining of the patient for a sufficient amount of time for diffusing said APIs through the mucosal lining of the oral cavity and into the bloodstream of the patient.

16. The method of claim 1, wherein the amounts of testosterone and estradiol in combination with the penetration enhancer deliver a bloodstream dosage that mimics a circadian rhythm and physiological pulsatile secretion of testosterone in the patient.

\* \* \* \* \*